US012741142B2

(12) United States Patent
Heo

(10) Patent No.: US 12,741,142 B2
(45) Date of Patent: Sep. 22, 2026

(54) TWS EARPHONE ASSEMBLY CAPABLE OF SELECTIVELY EXECUTING TES TREATMENT FUNCTION

(71) Applicant: MOBIFREN CO., LTD, Gumi-si (KR)

(72) Inventor: Ju Won Heo, Gumi-si (KR)

(73) Assignee: MOBIFREN CO., LTD, Gumi-si (KR)

( * ) Notice: Subject to any disclaimer, the term of this patent is extended or adjusted under 35 U.S.C. 154(b) by 151 days.

(21) Appl. No.: 18/527,743

(22) Filed: Dec. 4, 2023

(65) Prior Publication Data

US 2025/0177745 A1 Jun. 5, 2025

(51) Int. Cl.

*A61N 1/36* (2006.01)
*A61N 1/04* (2006.01)
*H04R 1/10* (2006.01)
*H04R 1/1025* (2026.01)
*H04R 5/033* (2006.01)

(52) U.S. Cl.

CPC ....... *A61N 1/36025* (2013.01); *A61N 1/0456* (2013.01); *A61N 1/36034* (2017.08); *H04R 1/1016* (2013.01); *H04R 1/1025* (2013.01); *H04R 1/1033* (2013.01); *H04R 1/1041* (2013.01); *H04R 5/033* (2013.01); *H04R 2420/07* (2013.01)

(58) Field of Classification Search

CPC .............. A61N 1/0456; A61N 1/36025; A61N 1/36034; H04R 1/1016; H04R 1/1033; H04R 1/1025; H04R 1/1041; H04R 2420/07; H04R 5/033

See application file for complete search history.

(56) References Cited

U.S. PATENT DOCUMENTS 9,686,603 B2 6/2017 Zheng et al.
11,324,916 B2 5/2022 Kranck
11,691,000 B2 7/2023 Heo
(Continued)

FOREIGN PATENT DOCUMENTS

CN 107847744 A 3/2018
CN 115253077 A 11/2022
(Continued)

OTHER PUBLICATIONS

Office Action issued on Sep. 30, 2024, for corresponding Korean Patent Application No. 10-2023-0191707, along with an English machine translation (7 pages).

(Continued)

*Primary Examiner* — Tammie K Marlen
(74) *Attorney, Agent, or Firm* — Hauptman Ham, LLP

(57) ABSTRACT

A true wireless stereo (TWS) earphone assembly includes a usual TWS circuit and a frequency generator configured to generate low-frequency signals for a transcranial electrical stimulation (TES) treatment and a TES signal amplifier configured to amplify the generated low-frequency signals, the frequency generator and the TES signal amplifier being provided on one of the pair of left and right earphones; an electrode provided on an outer surface of the housing of each of the pair of earphones for electrical contact with a skin of a user's ear; and a pair of female connectors provided in the housing of the pair of left and right earphones and a link cable that electrically and selectively connects and disconnects the pair of female connectors, so that an audio listening function and a TES treatment are executed selectively or together.

6 Claims, 12 Drawing Sheets

(56) References Cited

U.S. PATENT DOCUMENTS

| | | | |
|---|---|---|---|
| 2005/0165460 | A1 | 7/2005 | Erfan |
| 2009/0185699 | A1 | 7/2009 | Kim |
| 2015/0382115 | A1 | 12/2015 | Meskens et al. |
| 2017/0368329 | A1 | 12/2017 | Tyler et al. |
| 2019/0246982 | A1 | 8/2019 | Mackellar et al. |
| 2021/0046276 | A1 | 2/2021 | Papania |

FOREIGN PATENT DOCUMENTS

| | | | |
|---|---|---|---|
| EP | 2 455 130 | B1 | 10/2013 |
| JP | 3087449 | U | 8/2002 |
| JP | 7019646 | B2 | 2/2022 |
| KR | 10-1889021 | B1 | 8/2018 |
| KR | 10-2194266 | B1 | 12/2020 |
| KR | 10-2530052 | B1 | 5/2023 |
| KR | 10-2023-0080721 | A | 6/2023 |

OTHER PUBLICATIONS

Office Action dated Jan. 21, 2025, for corresponding Japanese Patent Application No. 2023-202292, along with an English machine translation (5 pages).

TWS EARPHONE ASSEMBLY CAPABLE OF SELECTIVELY EXECUTING TES TREATMENT FUNCTION

BACKGROUND OF THE INVENTION

1. Field of the Invention

The present disclosure relates to a true wireless stereo (TWS) earphone assembly capable of selectively executing a transcranial electrical stimulation (TES) treatment.

More specifically, the present disclosure provides a TWS earphone assembly configured to execute the TES treatment according to a user's choice by including, as an assembly member, an accessory that cooperates with a TWS earphone assembly in which a pair of left and right earphones are completely electrically separated from each other.

2. Description of the Prior Art

TWS earphone assemblies provide an audio unit in the form of a pair of left and right earphones, do not require separate electrical wiring between these earphones, and mainly receive and play back audio from an audio device according to the Bluetooth® communication protocol. Due to the convenience of use, compactness, and ease of portability, TWS earphone assemblies have become mainstream in the earphone market.

Conventionally, improvements have been made to TWS earphone assemblies with a focus on improving the audio of the earphones themselves, improving a driver unit and improving additional functions such as noise canceling and ambient sound listening functions, and improving an audio signal processing circuit.

The mainstream TWS earphone assemblies take a form in which a left earphone portion and a right earphone portion are completely separate from each other. Although a neckband-type earphone assembly, in which a pair of earphones with housings are connected to each other with various types of neckbands made of elastic wire or injection-molded material, or a sports-type earphone assembly, in which a pair of left and right earphone portions are connected to each other with a flexible lead wire, are also produced, in a preferred type of a TWS earphone assembly, a pair of left and right earphones are completely separated from each other.

Apart from the concept of TWS earphone assemblies based on their functional configurations, as a recent major trend, various electronic and electrical application products related to health has been produced with the main theme of physical and neuropsychological health and neuropsychological health.

This trend is inevitably required on the roadmap for future-oriented and human-oriented technological development, and forms a very important industrial area.

From a mental health perspective in modern society, issues such as insomnia, depression, ADHD, neurasthenia decreased concentration, and fatigue are becoming serious issues among modern individuals. In particular, in countries such as Russia and Northern Europe, where the winter season is long, there have been many efforts and attempts to improve the symptoms of climate-related mental health pathologies by applying electrical or magnetic stimulation to the human body.

Recently, through numerous papers and clinical trials, it has been theoretically and experimentally proven that treatment techniques using transcranial electrical stimulation (TES) or transcranial magnetic stimulation (TMS) have significant effects.

TMS and TES stimulation devices have already been widely available in many psychiatric hospitals in Korea. In particular, TES treatment has an extremely low risk of medical accidents due to its non-pharmacological, non-invasive, and non-addictive characteristics, and the active introduction of the treatment has been requested.

However, conventional TES and TMS devices for treating these mental health pathologies are equipped with a chair-like seat on which the patient sits and receives treatment, multiple electrode pads as electrodes, an electrical stimulation circuit, and a fine control panel, etc., in a single device. Accordingly, the devices were extremely expensive, and as a result, the devices could only be used in medium to large hospitals or larger institutions. In addition, there were problems in that it was very cumbersome to attach the electrode pads or the like to the patient and actually perform the treatment procedure, and the cost of the procedure is high due to exclusion from medical insurance coverage.

In addition, as a treatment with using TES, there is transcutaneous electrical nerve stimulation (TENS). Since the TENS also has the same concept as the TES in that it has a therapeutic function that produces neuropsychological effects, the TENS and the TES will be collectively described as "TES" below.

The TES treatment as a means of mental health treatment is applicable to commonly used headsets, earphones, or the like, and is likely to become established as a default function for the healing function of earphones and headsets in addition to audio listening and call functions, and has a very wide range of applications.

In order to apply these TES treatment functions to devices such as earphones and headsets rather than stationary devices installed in hospitals or the like, to widely distribute the devices to the general public in an inexpensive and easily portable form, the present inventor filed a patent application for a device illustrated in the circuit diagram of FIG. 2 and the external configuration view of FIG. 1 entitled "Bone Conduction Device with TES Treatment", and the application was granted a patent as Korean Patent No. 2194226.

The above-mentioned patent discloses a configuration that includes a pair of headsets in which a bone conduction unit for audio conduction is provided in a pair of headset-shaped headset portions and which includes metal electrodes for conducting a TES treatment signal to the pair of left and right headset portions and a TES treatment signal generation circuit within a Bluetooth® circuit, thereby implementing a TES treatment by causing low-frequency signals to pass through the human body, especially the head, between the pair of left and right headsets.

With this configuration, there is provided a means that allows a user to listen to audio or to actively and inexpensively enjoy the TES treatment by using the bone conduction unit, the TES signal generating circuit, and the electrodes selectively or simultaneously.

PRIOR ART DOCUMENTS

Patent Documents (Patent Document 0001) Korean Patent No. 2194266 (Dec. 16, 2020)

(Patent Document 0002) U.S. Pat. No. 9,686,603 (Jun. 20, 2017)

(Patent Document 0003) U.S. Patent Application Publication No. 2009/0185699 (Jul. 23, 2009)

(Patent Document 0004) U.S. Patent Application Publication No. 2015/0382115 (Dec. 31, 2015)

(Patent Document 0005) U.S. Patent Application Publication No. 2017/0368329 (Dec. 28, 2017)

SUMMARY OF THE INVENTION

In the prior art, headsets or earphones having the above-mentioned TES or TES treatment are known.

In particular, U.S. Patent Application Publication No 2015/0382115 (Dec. 31, 2015) of Patent Document 4 and U.S. Patent Application Publication 2017/0368329 (Dec. 28, 2017) of Patent Document 5 disclose a configuration in which TMS or TES is implemented in earphones configured to emit audio and a configuration in which patches are attached to the skin separately from earphones, which are technical ideas closest to the present disclosure but are different from the present disclosure in purpose, effect, and specific configurations.

The inventor's Korean Patent No. 2194266 described above provides a headset with a desirable TES treatment function using bone conduction, but it has been discovered that since audio conduction was limited to a headset type based on bone conduction, its applicability is limited, resulting in a lack of versatility.

The above configuration was inevitably adopted for the following reason: in order to implement the TES treatment, the human head must be sandwiched between the pair of separate left and right earphones of a TWS earphone assembly, and electrical signals must be applied to pass through the head over a certain area.

The technical idea of a TWS earphone assembly that can selectively execute the TES treatment of the present disclosure and the technical problems to be solved by the present disclosure will be described with reference to the inventor's Korean Patent No. 2194266, together with FIGS. 1 and 2.

The configuration disclosed in the inventor's Korean patent includes, as a circuit accommodated within one of the bone conduction headset housings 400, a Bluetooth® communication module 110, memory 115, a decoder 120, a digital-to-analog converter 125, an audio amplifier 130, bone conduction units 141 and 142, a frequency generator 150, a TES signal amplifier 160, electrodes 171 and 172, a user interface 180, and a controller 190.

Since audio data received through the Bluetooth® communication protocol or stored in the memory 115 is generally compressed digital data, the decoder 120 decodes the audio data input via the Bluetooth® communication module 110 or the audio data stored in the memory 115 and transmits the decoded audio data to the digital analog converter 125, and the digital-to-analog converter 125 converts the digital audio data from the decoder 120 into analog signals and outputs the analog audio signals to drive the left bone conduction unit 141 and the right bone conduction unit 142 so that audio is delivered to the human body.

With the above configuration, a frequency generator 150 is provided, and for the TES treatment function, for example, low-frequency signals between 1 and 150 Hz are generated and amplified by the TES signal amplifier 160, and TES signals are applied to the human body through electrodes 171 and 172 mounted on the headset housings. By manipulating the user interface 180, audio listening and treatment using TES signals can be enabled selectively or simultaneously.

In the inventor's Korean patent described above, the implementation is limited to a headset-type audio device, and the means for Bluetooth® communication and audio reproduction, the frequency generator 150, and the TES signal amplifier 160 are provided only in the specific housing 400 of one of the bone conduction headsets, and thus do not provide the function of a TWS earphone assembly.

In order to execute the TES treatment, low-frequency signals should pass (transdermally) across the human skin over a certain area from both ends, and as illustrated in FIG. 2, the TES signal amplifier 160 should be connected to the electrodes 171 and 172 of the housings via signal cables C1 and C2, respectively, which is not applicable to a TWS earphone assembly in which a pair of earphone units are completely electrically separated. Thus, it is unavoidable to adopt the above-described configuration of the headsets, and the disclosed technology is limited to bone conduction units rather than to general speaker units for audio generation.

It is believed that the most preferred embodiment of a TWS earphone assembly capable of executing the TES treatment function is to mainly use the TWS earphone assembly for listening to music and voice calls while walking, exercising, and working, which occupy most of the time that the TWS earphone assembly is used by the user, and that it is configured in the form of an optional additional device for the user to switch to the TES treatment only for a specific predetermined time (e.g., 15 minutes or 30 minutes).

In view of the foregoing, the present disclosure provides a TWS earphone assembly capable of selectively executing a TES treatment. The TWS earphone assembly may include, as a circuit configuration accommodated in each of the housings of a pair of left and right earphones which are electrically separated from each other, a Bluetooth® communication module, memory, a decoder, a digital-to-analog converter, an audio amplifier, a speaker unit, and a controller controlled by a user interface, the TWS earphone assembly further including: a frequency generator configured to generate low-frequency signals for TES treatment and a TES signal amplifier configured to amplify the generated low-frequency signals, the frequency generator and the TES signal amplifier being provided on one of the pair of left and right earphones; an electrode provided on an outer surface of the housing of each of the pair of left and right earphones for electrical contact with the skin of a user's ear; and a pair of female connectors provided in the housing of the pair of left and right earphones and a link cable that electrically and selectively connects and disconnects the pair of female connectors, wherein, when the link cable is released from the pair of earphones, the pair of earphones may play back audio as TWS earphones, or when the link cable electrically connects the pair of earphones, depending on the user's choice, the pair of earphones may conduct the generated low-frequency signals between the separated electrodes, thereby executing only the TES treatment or simultaneously performing the TES treatment and the audio playback function.

A TWS earphone assembly may include, as a circuit configuration accommodated in each of the housings of a pair of left and right earphones which are electrically separated from each other, a Bluetooth® communication module, memory, a decoder, a digital-to-analog converter, an audio amplifier, a speaker unit, and a controller controlled by a user interface, the TWS earphone assembly further including: a pair of female connectors provided in the housing of the pair of left and right earphones and a link cable that electrically and selectively connects and disconnects the pair of female connectors; an electrode further provided on an outer surface of the housing of each of the pair of left and right earphones for electrical contact with a skin of the user's ear; and a housing that accommodates a frequency generator configured to generate low-frequency signals for TES treatment and a TES signal amplifier configured to amplify the generated low-frequency signals and that is separated from the circuit of one of the pair of left and right earphones, the housing being provided on the link cable, wherein the pair of left and right earphones play back audio as TWS earphones when the link cable is released, or when the link cable is connected, depending on the user's choice, the pair of earphones conduct the generated low-frequency signals between the separated electrodes, thereby executing only the TES treatment or simultaneously performing the TES treatment and the audio playback function.

A TWS earphone assembly capable of selectively executing a TES treatment according to the present disclosure is easily applicable to a conventional TWS earphone assembly and provides a means for performing mental health treatment simply and inexpensively.

Furthermore, the present disclosure provides a TWS earphone assembly capable of maximizing the treatment effect by increasing portability and usability.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, the configurations and operations of a wireless earphone assembly according to embodiments of the present disclosure capable of selectively executing a TES treatment and a wireless earphone assembly according to modifications of the embodiments will be described in detail with reference to the accompanying drawings.

Figure 1:
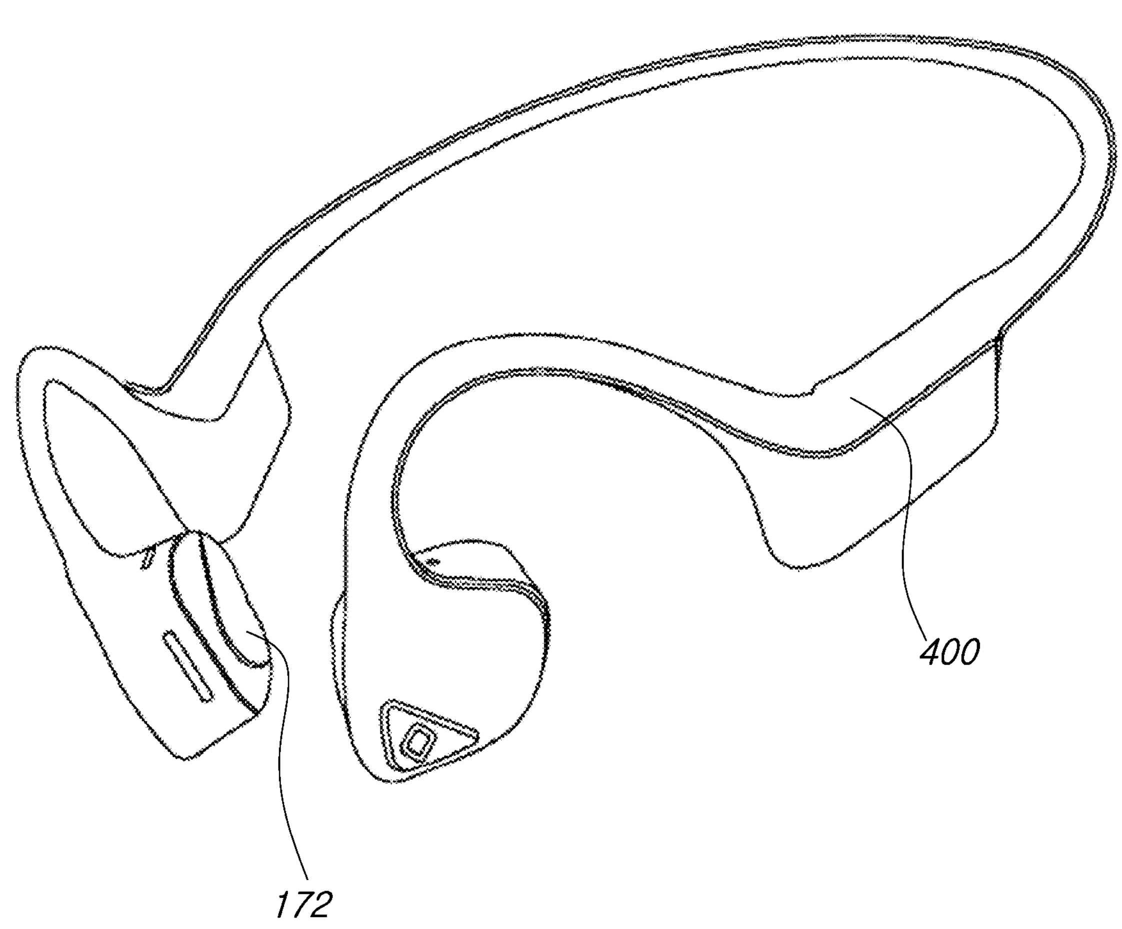
FIG. 1 is a perspective view illustrating the 1 external view of a conventional headset known in the art.
Figure 2:
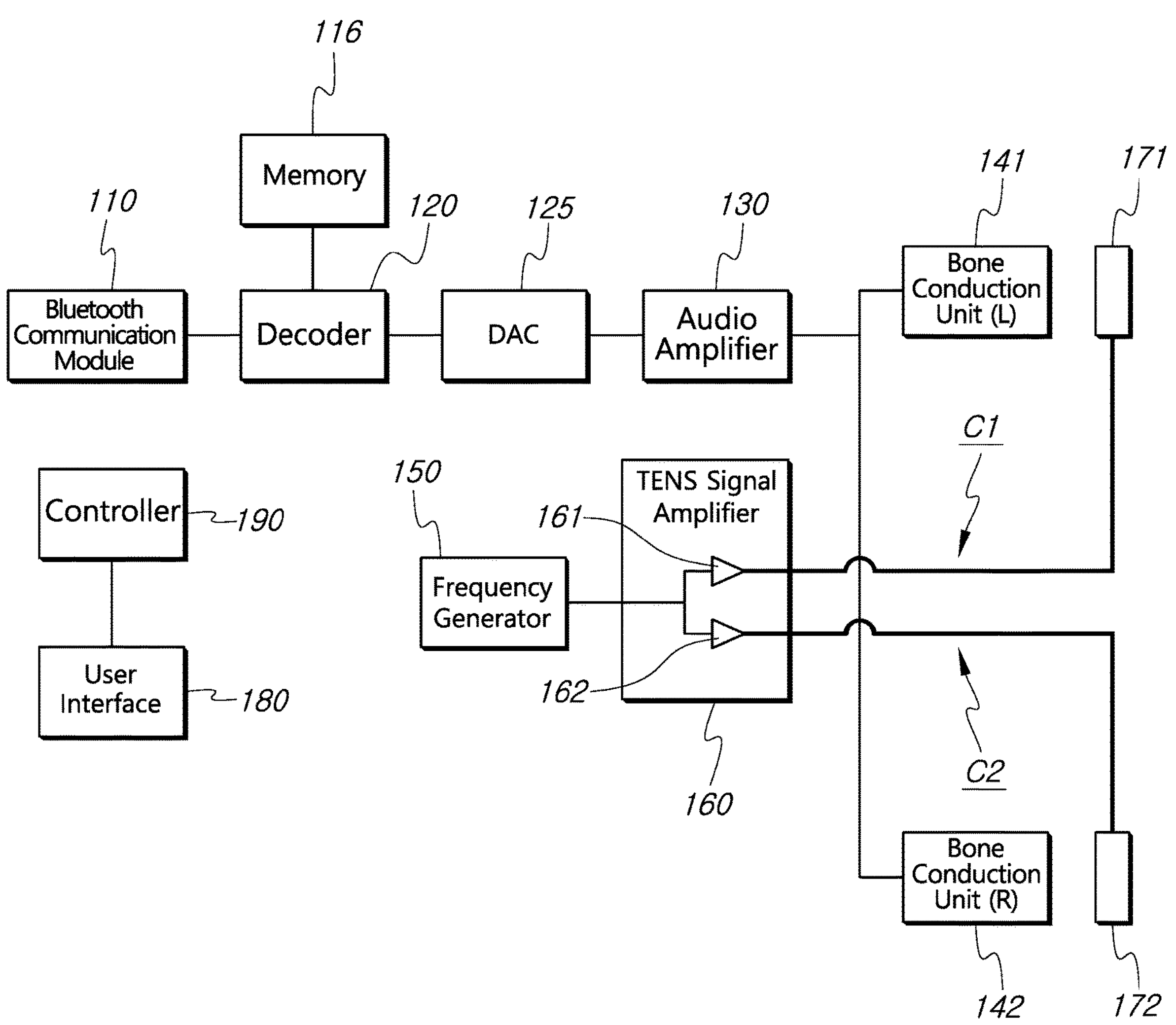
FIG. 2 is a circuit diagram known in the art, which may be applied to the headset of FIG. 1.
Figure 3:
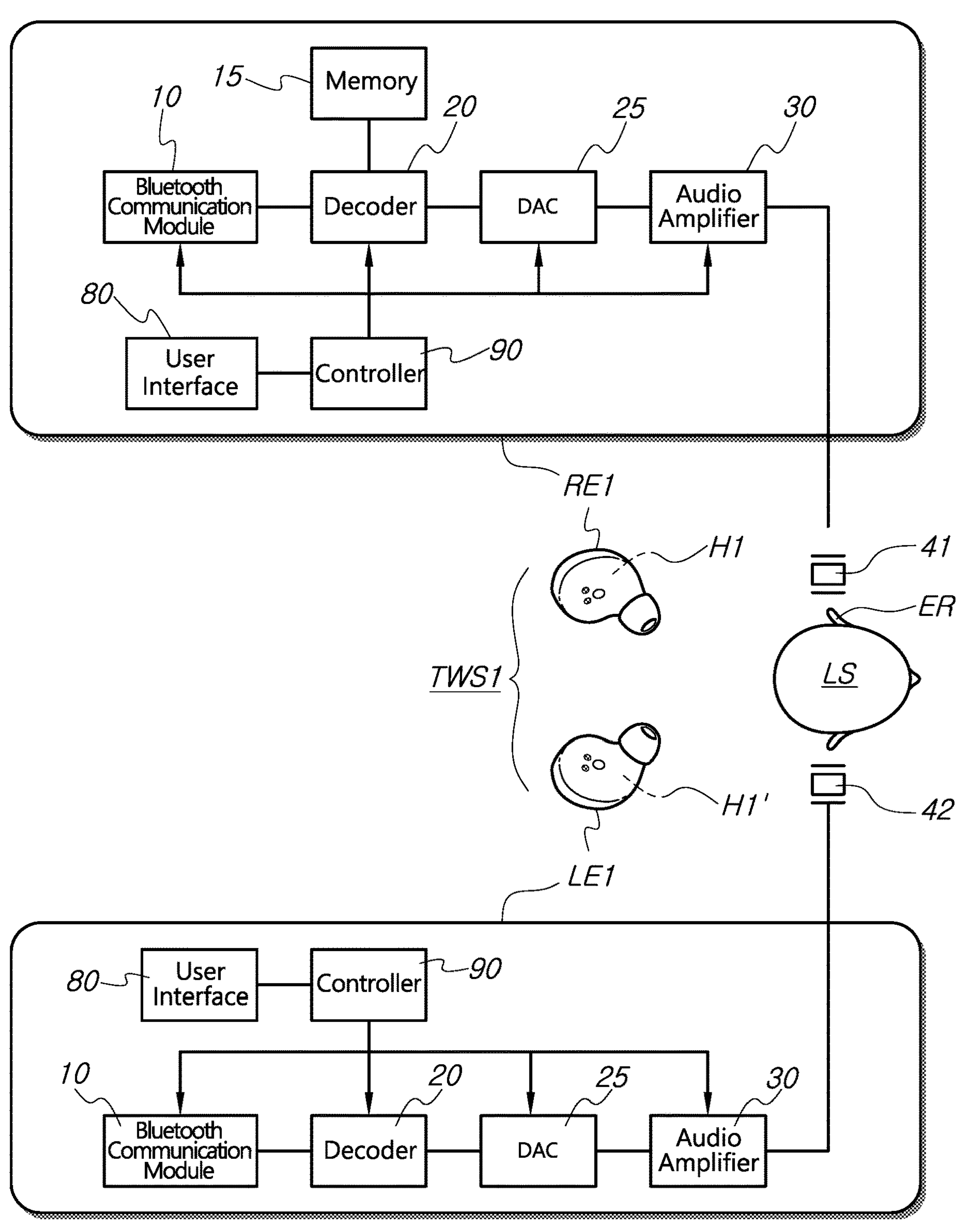
FIG. 3 is a block diagram of a circuit of a conventional TWS earphone assembly.

FIG. 3 is a block diagram of a circuit illustrating a conventional TWS earphone assembly, and FIGS. 4 to 14 illustrate embodiments of the present disclosure and modifications thereof, which will be described sequentially and together below.

In the following description of the embodiments of the present disclosure, when referring to members located in the same positions and performing the same function, the same reference numerals will be assigned even in different embodiments.

Figure 4:
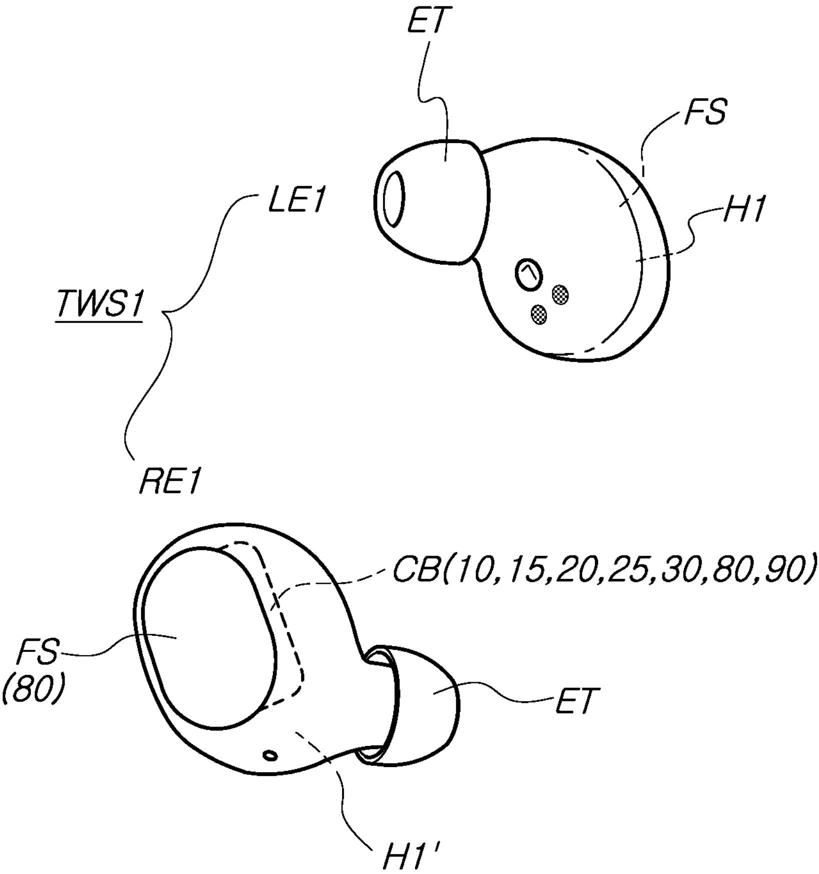
FIG. 4 is a perspective view illustrating the external view of a conventional TWS earphone assembly.

As shown in the block diagram of the circuit configuration of FIG. 3 and the exemplary perspective view of FIG. 4, a conventional TWS earphone assembly TWS1 has Bluetooth® communication modules 10, memories 15, decoders 20, digital-to-analog converters 25, audio amplifiers 30, and speaker units 41 and 42, as circuit configurations implemented on circuit boards CB which are respectively accommodated in housings H1 and H1' of a pair of earphones RE1 and LE1, that are completely separated from each other on the left and right.

In addition, under the control of a controller 90, which is operated and controlled by a user interface 80, which is a multi-function switch FS including a touch switch, a membrane switch, and the like, audio signals including call signals from the decoders 20 are played back to the speaker units 41 and 42 through the digital-to-analog converters 25 and the audio amplifiers 30.

A user LS as a listener listens to audio from the speaker units 41 and 42 of the pair of left and right earphones RE1 and RE2 of the stereo TWS earphone assembly TWS1, wherein the left and right earphones RE1 and LE1 are completely electrically separated, and with this configuration, the TES treatment, which can be implemented only when electrical signals penetrate a certain area of the human body, especially the head, cannot be used.

In view of these points, the present disclosure provides a TWS earphone assemblies as an earphone assembly in various forms configured to additionally and selectively provide a TES treatment so that a user LS can selectively use the TES treatment.

First Embodiment

Figure 5:
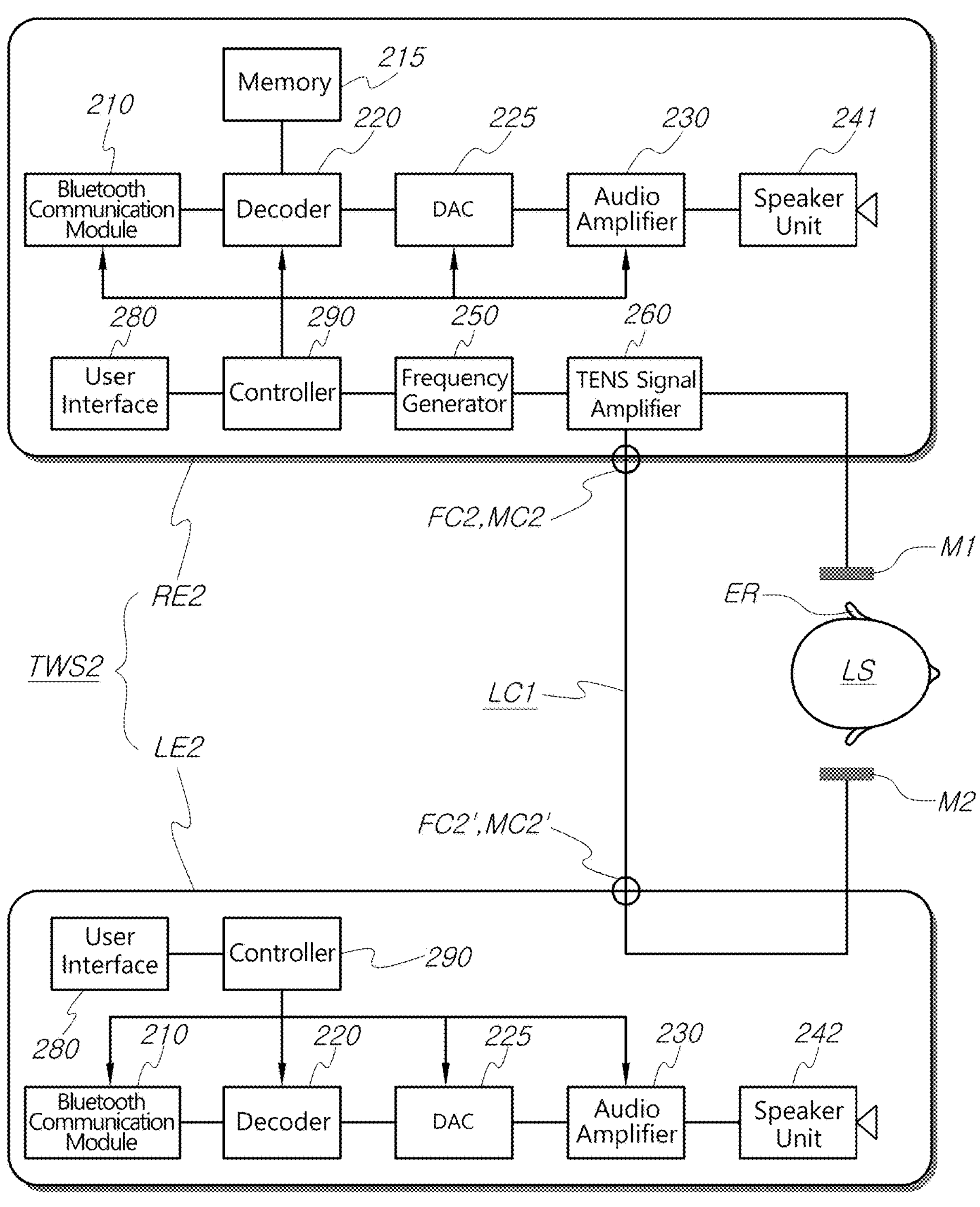
FIG. 5 is a block diagram illustrating the circuit configuration of a TWS earphone assembly capable of selectively executing a TES treatment according to a first embodiment of the present disclosure.
Figure 6:
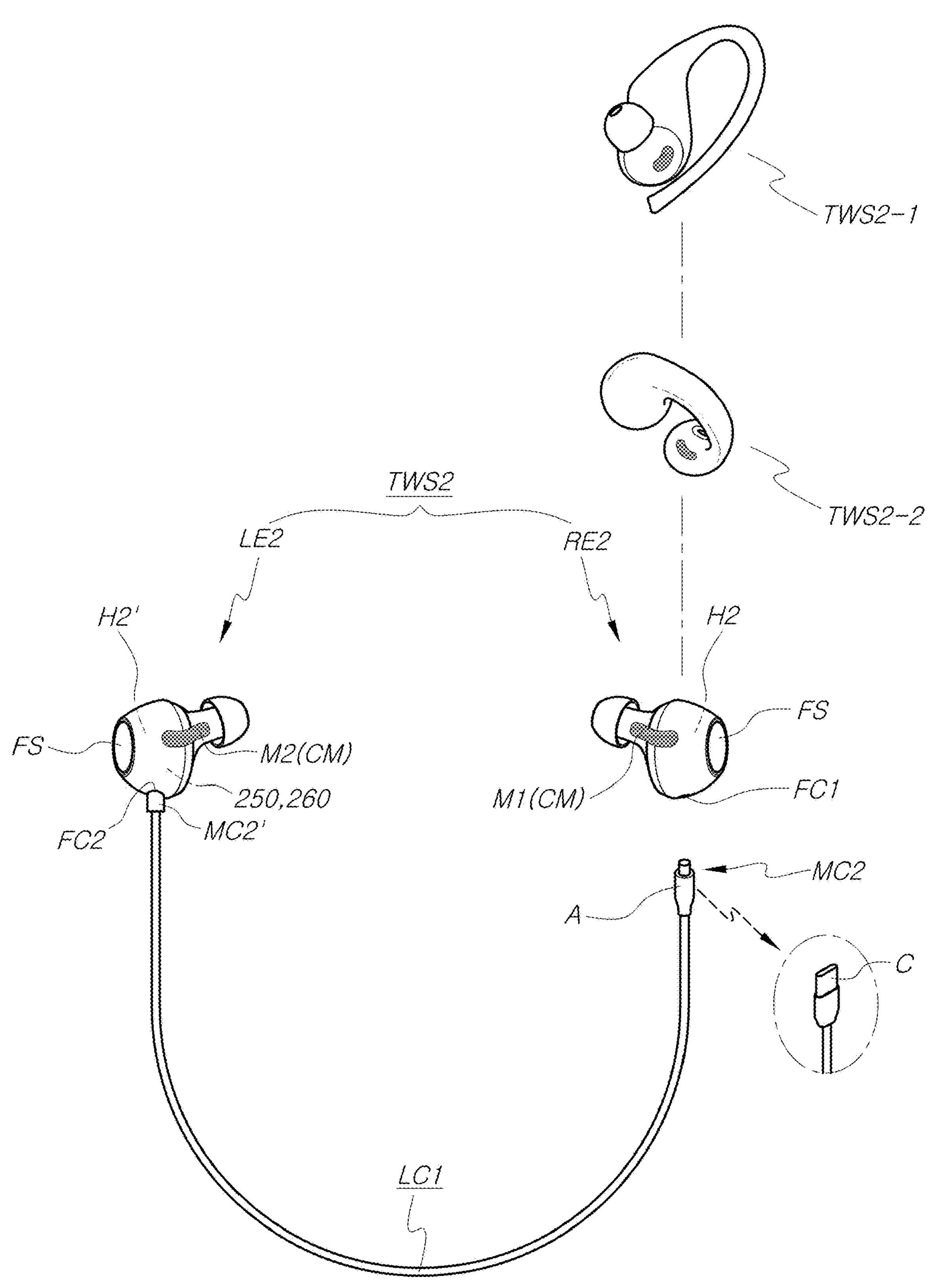
FIG. 6 is a perspective view illustrating the external view of an exemplary TWS earphone assembly in which the circuit configuration of the first embodiment of the present disclosure of FIG. 5 is implemented.

As illustrated in the block diagram of FIG. 5 and the external perspective view of FIG. 6, a TWS earphone assembly TWS2 capable of selectively executing a TES treatment according to a first embodiment of the present disclosure includes: Bluetooth® communication modules 210; memories 215; decoders 220; digital-to-analog converters 225; audio amplifiers 230; speaker units 241 and 242 which are audio drive units; and controllers 290 operated by user interfaces 280 as circuits accommodated respectively in housings H2 and H2' of a pair of left and right earphones RE2 and LE2 as in the conventional earphone assembly TWS1.

As is well known to those skilled in the art, one of the circuits accommodated in the housings H2 and H2' of the pair of left and right earphones RE2, LE2 further includes, in addition to the above-described audio data reception and playback circuit, a frequency generator 250 that is electrically connected to the controller 290, which is operated and controlled by the user interface 280 and generates low-frequency signals to implement the TES treatment, and a TES signal amplifier 260 that amplifies the generated low-frequency signals.

The TES signal amplifier 260 allows a user to vary the degree of amplification through the user interface 280, and the frequency generator may be configured as a separate circuit unit as described above, but the controller 290 may directly generate low-frequency signals.

Figure 7:
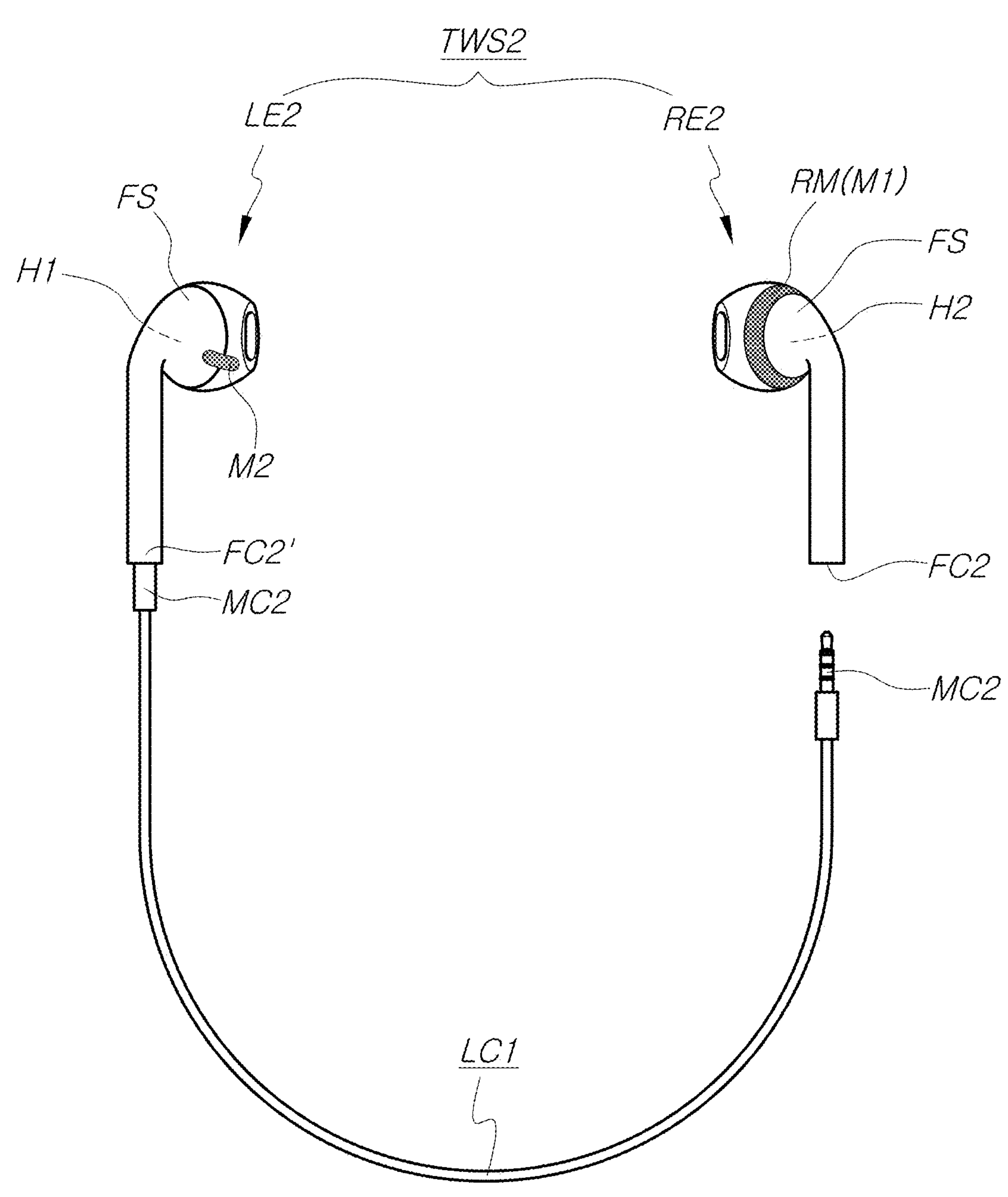
FIG. 7 is a perspective view illustrating the external view of another exemplary TWS earphone assembly in which the circuit configuration of the first embodiment of the present disclosure of FIG. 5 is implemented.

In addition to including speaker units 241 and 242 in the housings H2 and H2' of the pair of left and right earphones RE2 and LE2 as illustrated in FIGS. 6 and 7, the pair of earphones RE2 and LE2 may be products designed with various shapes such as an ear-hanger-type earphone TWS2-1 or an ear-clip TWS2-2 mounted on an earlobe, as illustrated in FIG. 6.

In the present disclosure, in order to facilitate connection with the skin of the outer ear and inner ear in the ears ER of a user LS and further implement a complete electrical connection, electrodes M1 and M2 having various shapes and materials and connected to portions of the skin surface of the ears ER of the user LS are further provided on the outer surface of each of the housings H2 and H2' of the earphones.

The electrodes M1 and M2 may have a shape suitable for connection to the skin of the outer ears and inner ears of the ears ER of the user, such as electrodes M1 and M2 (CM) having partial contact areas or ring-shaped electrodes M1 and M2 (RM) as illustrated in the left portions of FIGS. 6 and 7, and may be metal electrodes plated with various materials, such as stainless steel, chrome, and gold that are harmless to the human body, corrosion resistant, and highly conductive.

As described above, the low-frequency signals for a TES treatment from the frequency generator 250 for low-frequency signal generation and the TES signal amplifier 260 can be effective in the treatment only when they are electrically connected to the electrodes M1 and M2 of the housings H2 and H2' of the pair of left and right earphones RE2 and LE2.

In order to implement a selective and intentional TES treatment selected by the user LS, electrical signals from the TES signal amplifier 260 accommodated in the housing H2 or H2' of one of the pair of left and right earphones RE2 and LE2 which are electrically separated from each other should be connected to the electrodes M1 or M2 of the other earphones RE2 and LE2.

In order to implement this and to provide a complete TWS earphone assembly TWS2, as illustrated in FIGS. 5 to 7, in the first embodiment of the present disclosure, female connectors FC2 and FC2' selected from various types of connectors are provided on the housings H2 and H2' of the pair of left and right earphones RE2 and LE2, respectively, and a link cable LC1 for electrically and selectively connecting the pair of female connectors FC2 and FC2' is configured as an assembly member provided together with the pair of earphones RE2 and LE2.

Of course, the pair of earphones RE2 and LE2 may have various external shapes, such as the hanger-type earphone TWS2-1 or the ear-clip TWS2-2 mounted on the earlobe, as illustrated in FIG. 6.

The link cable (LC1) may be a flexible, conventional resin-coated or fiber-coated cable for electrical conduction and, if necessary, may be configured in the form of a steel band, a synthetic resin band, or a rubber band that accommodates one or more wires therein along the longitudinal direction.

Furthermore, the link cable may be a neckband produced by injection molding into a predetermined form as in a modification to be described later and another embodiment of FIG. 9.

At opposite ends of the link cable LC1, a pair of male connectors MC2 and MC2' are provided as means for forming electrical connection to the pair of female connectors FC2 and FC2' according to a user's choice.

The female connectors FC2 and FC2' and male connectors MC2 and MC2' may be in the form of a typical jack-plug A as a connection element for connecting and disconnecting electrical signals, as illustrated in the right portion of FIG. 6, and may be terminal connectors corresponding to commonly used USB-C type terminals C and magnetic contact terminals, and any configuration that enables electrical connection by mechanical means may be adopted.

The TWS earphone assembly TWS2 of the first embodiment is capable of adopting various operating modes in transition between a normal audio and voice listening function and a TES treatment.

For example, when music playback is controlled by a multi-function switch FS while the link cable LC1 is inserted into the earphones RE2 and LE2, the TES treatment is automatically activated, or even if the link cable LC1 is inserted into the earphones RE2 and LE2, the earphones RE2 and LE2 are activated by manipulating the user interface 280, which is a multi-function switch FS, to enter the TES treatment.

Various types of operations can be programmed into the controller 90, and operation settings may be made through the multi-function switch FS of the user interface 80 of any one of the earphones RE2 and LE2, for example, the right earphone RE2, as follows: touching twice starts the TES treatment, touching twice the multi-function switch FS during operation stops the TES treatment, a short touch on the multi-function switch FS of the right earphone RE2 increases the volume, a long touch on the multi-function switch FS of the right earphone RE2 increases the level of TES signal, a short touch on the multi-function switch FS of the left earphone LE2 decreases the volume, a long touch on the multi-function switch FS of the left earphone LE2 decreases the level of the TES signal, and so on.

In addition, depending on whether the link cable LC1 is inserted into the earphones RE2 and LE2, the appropriate operating mode of the earphones RE2 and LE2 can be automatically or manually controlled.

Figure 8:
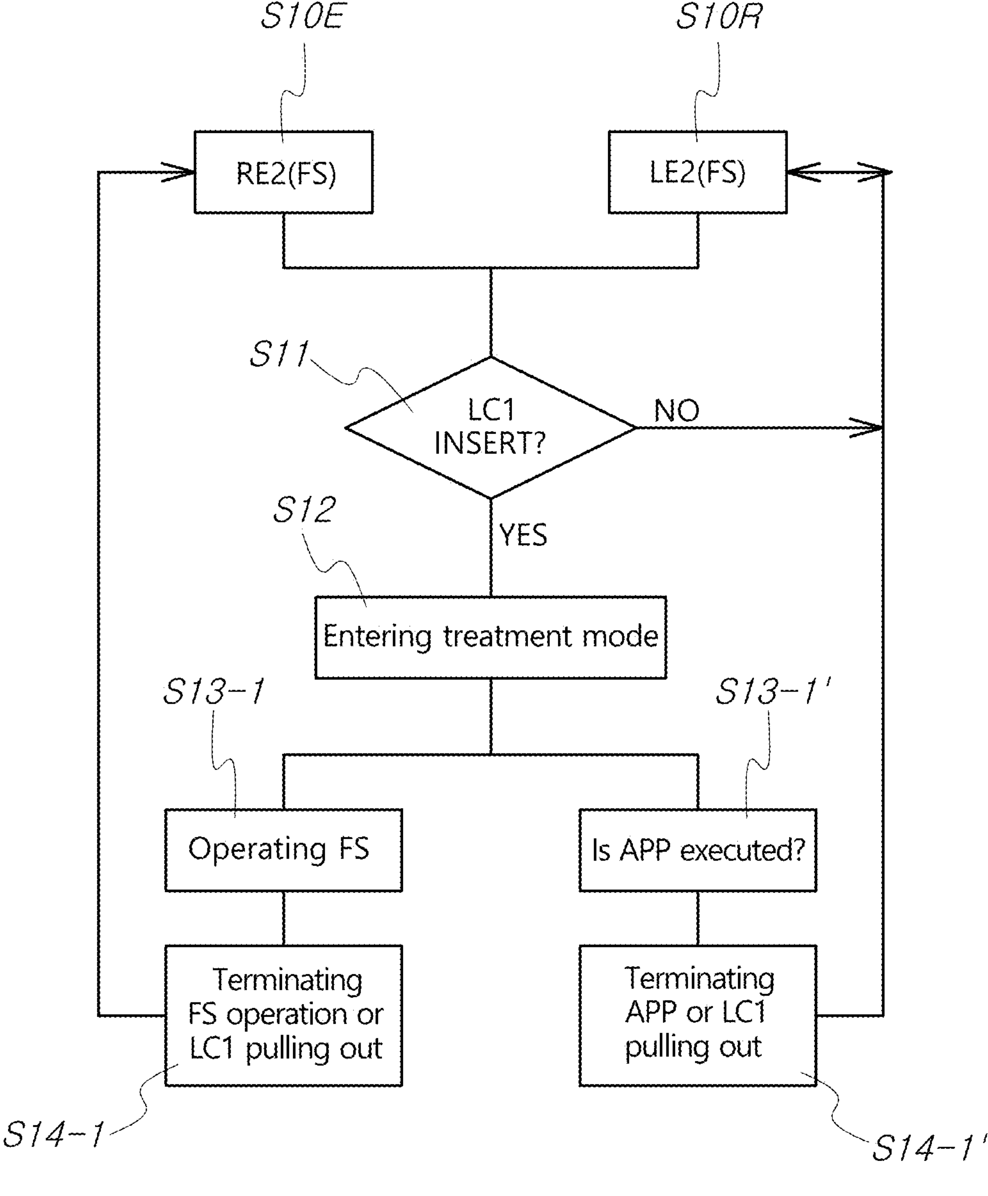
FIG. 8 is a flowchart illustrating the operating mode of the first embodiment of the present disclosure in FIG. 5.

As illustrated in FIG. 8, the earphones RE2 and LE2 of the TWS earphone assembly TWS2 are put into a user LS use mode, i.e., a general use mode as audio and voice listening stages S10R and S10E in which the earphones RE2 and LE2 of the TWS earphone assembly are used for listening to music or waiting for a call.

From the audio and voice listening step S10 of this general use mode, in order to use the TES treatment, when a user LS connects the male connectors MC2 and MC2' on the opposite ends of the link cable LC1 into the female connectors FC2 and FC2' of the pair of left and right earphones RE2 and LE2 in order to use the TES treatment, the controller 90 detects this state and determines whether the link cable LC1 is connected in the link cable LC1 insertion determination step S11, and when it is determined that the link cable LC1 is not inserted into the earphones RE2 and LE2 (NO), the controller 90 returns to the audio and voice listening step S10 in which the TWS earphone assembly is in the general use mode.

When it is determined that the link cable LC1 is inserted into the pair of left and right earphones RE2 and LE2 (YES), the controller 90 enters a TES treatment mode S12), and an interface operation step S13-1 in which the user LS operates the user interface 280 of the TES treatment of the earphone RE2 and LE2 (that is, operating the multi-function switch FS of one of the left and right earphones RE2 and LE2 or an application execution operation step S13-1' in which an application installed on a smartphone is executed by using Bluetooth® is performed to use the TES treatment.

When it is desired to terminate the TES treatment, the process returns to the audio and voice listening step S10 after passing through a step in which the user LS terminates the TES treatment by manipulating the multi-function switch FS, the step S14-1 in which the link cable LC1 is removed from the earphones RE2 and LE2, the step in which an application is terminated by a user operation, or the step S14-1' in which the link cable LC1 is removed from the earphones RE2 and LE2.

The control mode described above is an example, and of course, various complex controls are possible.

In the above-described embodiment, the TWS earphone assembly TWS2 of the present disclosure may be mainly used to receive YouTube or self-stored audio sources through Bluetooth® communication from various devices (a smartphone, a PC, or the like) according to the Bluetooth® communication protocol.

In this case, a user must select an audio source and then use the TES treatment while playing back music, which may cause inconvenience to those who are not good at operating machines. Therefore, when control is performed in conjunction with an application, audio source files (healing music with healing effects or the like) are provided to the application by default, when the application is installed, when the FS button is manipulated, or when control is performed by the application, the TES treatment is executed with the music provided in the application.

It would be desirable to create a music source for an application so that a user can add or delete his/her favorite music.

Of course, by providing audio source files such as MP3 files (healing music with healing effects, etc.) in the remaining storage space of the built-in memory 215 or a separate audio source memory (not illustrated) at the time of initial shipment from a factory, the user may listen to music for healing without using a separate external device at the time of using the treatment.

Furthermore, it is also possible to allow the user LS to download audio source files of MP3 files or the like stored in memory from a site provided by the manufacturer.

Modification of First Embodiment

Figure 9:
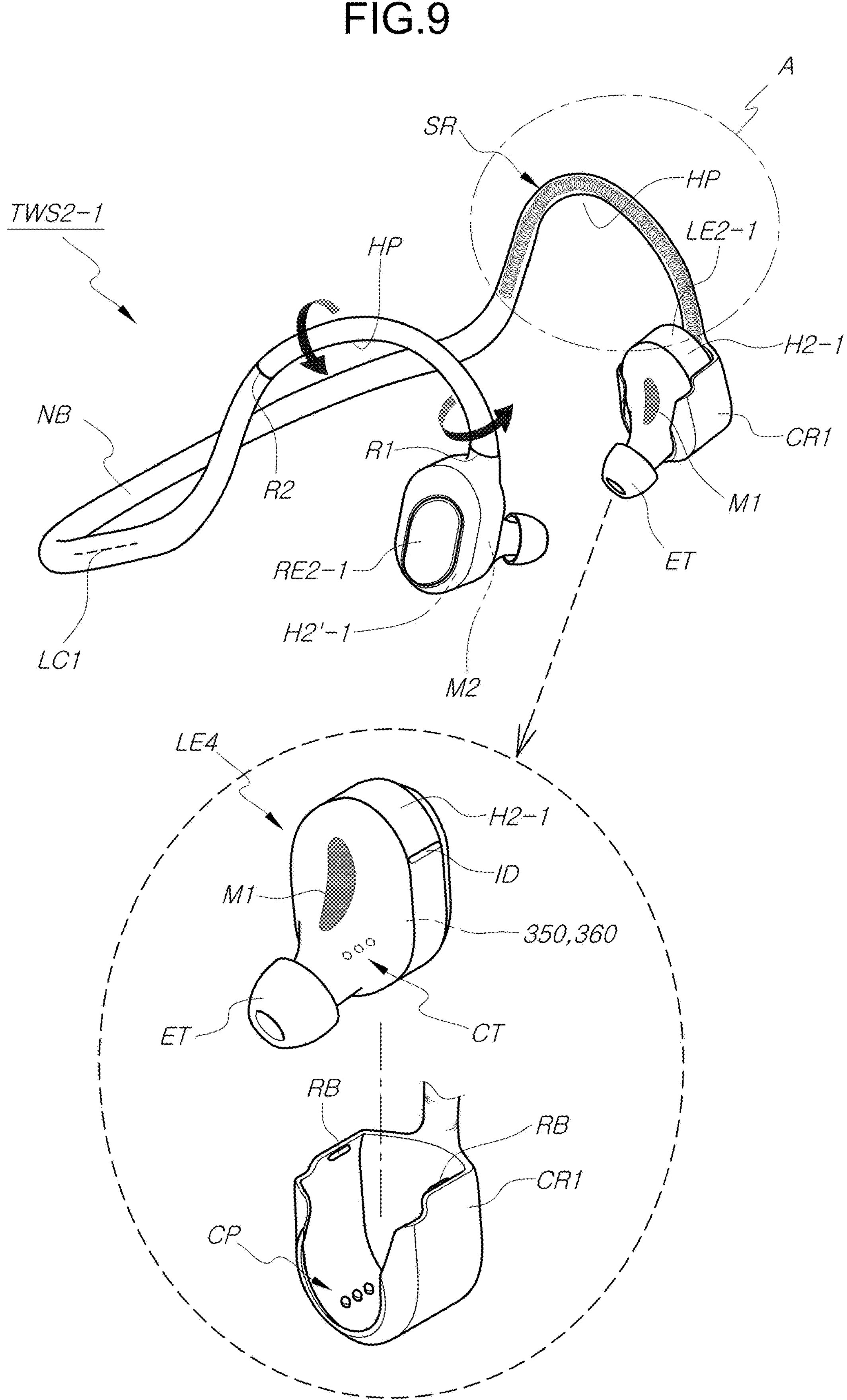
FIG. 9 is a perspective view illustrating the external view of another exemplary TWS earphone assembly of a modification of the first embodiment of the present disclosure.

As illustrated in FIG. 9, in a modification of the first embodiment of the present disclosure, the TWS earphone assembly TWS2-1 is configured to accommodate a link cable LC1-1 inside a cradle-shaped neckband structure NB that is injection-molded, instead of the link cable LC1 of the first embodiment.

The pair of left and right earphones RE2-1 and LE2-1 of the earphone assembly TWS2-1 of the modification of the first embodiment have almost the same actual configuration as those of the first embodiment.

As circuits accommodated respectively in the housings H2-1 and H2'-1 of the pair of earphones RE2-1 and LE2-1, Bluetooth® communication modules 210, memories 215, decoders 220, digital-to-analog converters 225, audio amplifiers 230, speaker units 241 and 242 which are audio driver units, and controllers 290 operated by user interfaces 280, are provided in the same manner as the first embodiment illustrated in FIG. 5.

In the housings H2-1 and H2'-1 of the pair of left and right earphones RE2-1 and LE2-1, in addition to the speaker units 241 and 242, electrodes M1 and M2 are installed on the outer surfaces of the housings H2-1 and H2'-1 in the same manner as in the first and second embodiments to be brought into contact with the skin of the outer ear and inner ears of the user LS.

One of the above-mentioned pair of left and right earphones RE2-1 and LE2-1 is equipped with a frequency generator 250 for low-frequency wave generation for a TES treatment and a TES signal amplifier 260 for amplification on the circuit thereof.

In the TWS earphone assembly TWS2-1 of the modification of the first embodiment, the pair of left and right earphones RE2-1 and LE2-1 include housing-shaped cradles capable of selectively receiving the earphones, respectively, and the respective cradles are molded and provided to be suspended from the left and right ears of a user LS by a neckband NB containing the link cable LC2-1 therein.

As illustrated in FIG. 9, the neckband NB may be an injection-molded product that has suspension portions HP, which are curved to be suitable for seating on and hanging from the left and right ears of the user LS, or may be a cable-shaped product having a spring SR covered with an injection molded flexible synthetic resin or rubber sheath to be freely bent into any shape by the user as illustrated in the enlarged view of part A adjacent to the earphone LE2-1 for the left ear ER of the user LS in FIG. 9.

The neckband NB is provided with one or more rotatable joint portions R1 and R2 at one or more locations preferably at two locations at the end portions of the neckband NB, as illustrated in the left portion of FIG. 9, whereby eartips ET protruding from the housings H2-1 and H2'-1 of the pair of left and right earphones RE2-1 and LE2-1 can be inserted into the correct positions in the ears ER of the user LS.

Alternatively, as illustrated in the enlarged view of the part A in the right portion of FIG. 9, the neckband NB has a spring covered with an injection-molded flexible synthetic resin or rubber sheath to be freely bent into any shape, thereby allowing the earphones to be inserted into the ears ER of the user LS in the optimal shape at the optimal positions.

Earphone cradles CR1 and CR2 in which a pair of left and right earphones RE2-1 and LE2-1 are received are provided in a housing shaped structure at the opposite ends of the neckband NB, respectively, wherein, as illustrated in FIG. 9, the earphone cradles CR1 and CR2 may be hollow bodies in which the earphones RE2-1 and LE2-1 are fixed by one or more engagement pieces RB geometrically fitted into fitting grooves ID provided on the earphones RE2-1 and LE2-1 as indentations.

The earphones RE2-1 and LE2-1 may be provided with various shapes and numbers of the fitting grooves ID and the earphone cradles CR1 and CR2 may be provided with various shapes and numbers of engagement pieces RB.

Alternatively, magnets (not illustrated) may be provided on the earphones RE2-1 and LE2-1 and the earphone cradles CR1 and CR2, respectively.

In addition to the mechanical fitting and fixing method of the earphones RE2-1 and LE2-1 and the earphone cradles CR1 and CR2 as described above, the earphones RE2-1 and LE2-1 may be fixed in place inside the earphone cradles CR1 and CR2 by causing sets of magnets (not shown) with strong magnetic force, such as neodymium magnets, to be detachably attached to each other, wherein the magnets are provided on the bottom surfaces of the earphones RE2-1 and LE2-1 and the inner surfaces of the earphone cradles CR1 and CR2, respectively.

Inside the earphone cradles CR1 and CR2, a plurality of connection pins CP and connection terminals CT as typical contact-type terminals for electrically connect the link cable LC1 accommodated within the neckband NB to the earphones RE2-1 and LE2-1 are provided.

Second Embodiment

Figure 10:
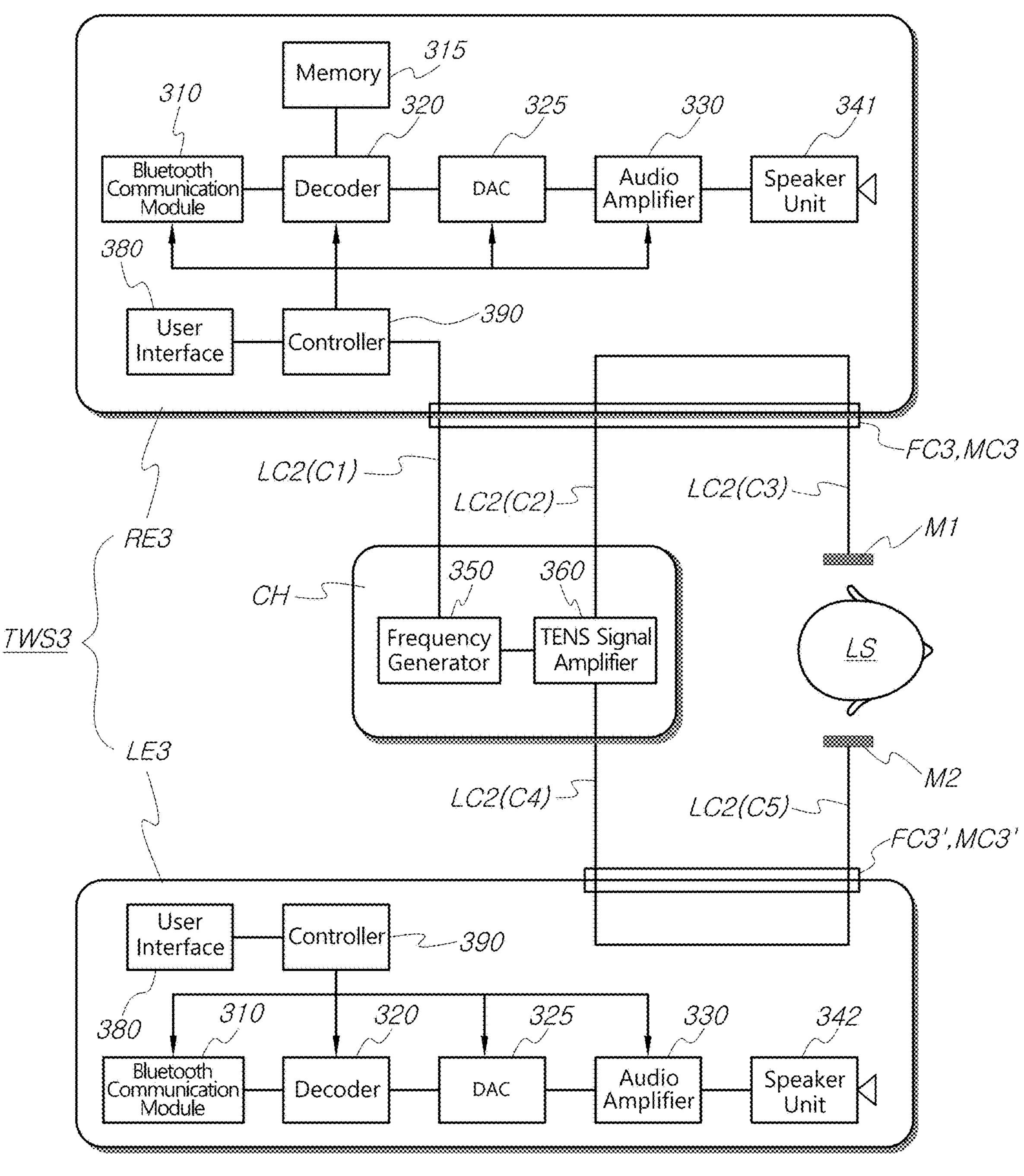
FIG. 10 is a block diagram illustrating the circuit configuration of a TWS earphone assembly of capable of selectively executing a TES treatment according to a second embodiment of the present disclosure.

In a second embodiment of the present disclosure and a modification thereof, as illustrated in FIGS. 10, in order to provide a TWS earphone assembly TWS3, as circuits accommodated respectively in the housings H3 and H3' of a pair of left and right earphones RE3 and LE3, Bluetooth® communication modules 310, memories 315, decoders 320, digital-to-analog converters 325, audio amplifiers 330, speaker units 341, 342, controllers 390 operated by user interfaces 380, and speaker units 341 and 342, which are audio drive units, are also provided in the same manner as the conventional configuration.

In addition to the above configuration, the TWS earphone assembly TWS3 further includes a frequency generator 350 for generating low frequency signals and a TES signal amplifier 360 for amplification, which are separated and isolated from the circuits, which are respectively accommodated in the housings H3 and H3' of the pair of left and right earphones RE3 and LE3, and are signal-connected to the controller 390 of a circuit which is accommodated in a housing H3 or H3' of one of the left and right earphones RE3 and LE3.

Furthermore, in addition to the speaker units 341 and 342, in the housings H3 and H3' of the pair of left and right earphones RE3 and LE3 of the TWS earphone assembly TWS3, electrodes M1 and M2 are installed on the outer surfaces of the housings H3 and H3' in the same manner as in the first embodiment to be brought into contact with the skin of the outer ear and inner ears of the user LS.

Furthermore, female connectors FC3 and FC3' are provided on the housings H3 and H3' of the pair of left and right earphones RE3 and LE3 of the TWS earphone assembly TWS3, respectively, and are provided as an assembly member in which a plurality of inner cables C1, C2, C3, C4, and C5 (see FIG. 11) are built in a single link cable LC2 to electrically and selectively connect the pair of connectors CN3 and CN3'.

A pair of electrically conductive male connectors MC3 and MC3' are provided at opposite ends of the link cable LC2 in the same form as in the first embodiment.

Figure 12:
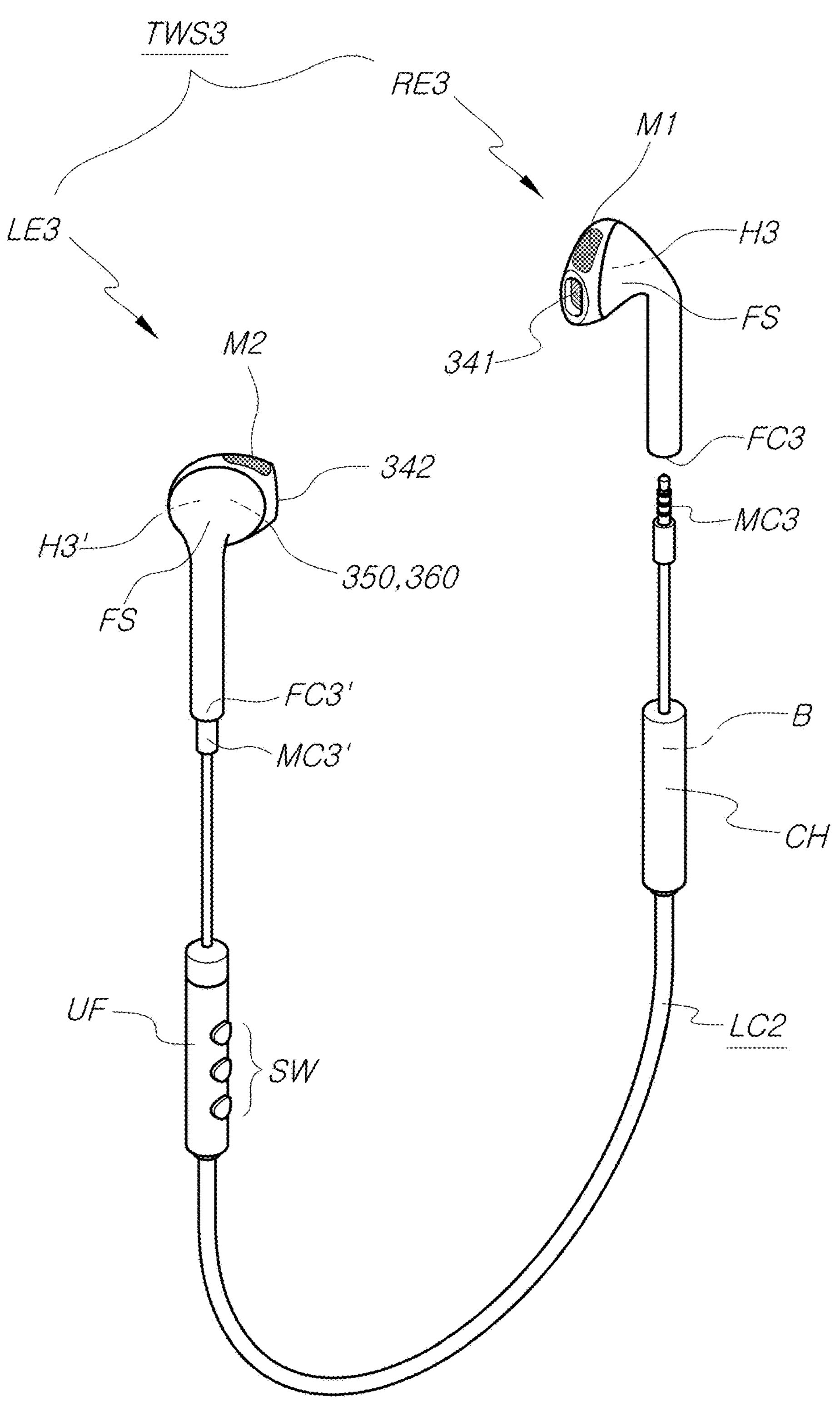
FIG. 12 is a perspective view illustrating the external view of an exemplary TWS earphone assembly in which the circuit configurations of the second embodiment of the present disclosure and the modification of FIG. 11 are implemented.

The frequency generator 350 for low-frequency generation and the TES signal amplifier 360 for amplification, which are signal-connected to a controller 390 of one of the circuits accommodated in the housings H3 and H3' of the pair of left and right earphones RE3 and LE3 of the TWS earphone assembly TWS3 and separated from each other and provided outside the housing H3 or H3' of one of the pair of left and right earphones RE3 and LE3 as illustrated in FIG. 12 may be provided on a separate circuit accommodated inside a cable housing CH in the form of a long housing provided at an appropriate position in the middle of the link cable CL2.

As illustrated in the left portion of FIG. 12 illustrating the earphone LE3, in the case where one of the earphones RE3 and LE3 of the TWS earphone assembly TWS3 is connected to the cable housing CH that accommodates the frequency generator 350 and the TES signal amplifier 360, and it is recognized that a TES treatment is executed by the switch SW for the user interface UF, the user interface UF for controlling the playback of audio source files (healing music with healing effects or the like) stored in an application of a mobile phone may be further provided as a housing having an operation switch SW for controlling both audio signals and signals for the TES treatment in addition to the user interface 380 for audio manipulation of the circuit outside the pair of earphones RE3 and LE3.

In this case, it is provided as an assembly member that electrically connects the pair of earphones RE3 and LE3 with a single link cable LC2 containing multiple inner cables C1, C2, C3, C4, and C5.

In the above configuration, when the link cable LC2 is separated from the pair of left and right earphones RE3 and LE3 of the present embodiment, the frequency generator 350 for generating low-frequency signals for a TES treatment and the TES signal amplifier 360 for amplification constitute a circuit completely separated from the pair of left and right earphones RE3 and LE3.

In this state, the user can use the earphone assembly TWS3 as TWS earphones, thereby ensuring miniaturization and weight reduction of the pair of earphones RE3 and LE3.

Figure 11:
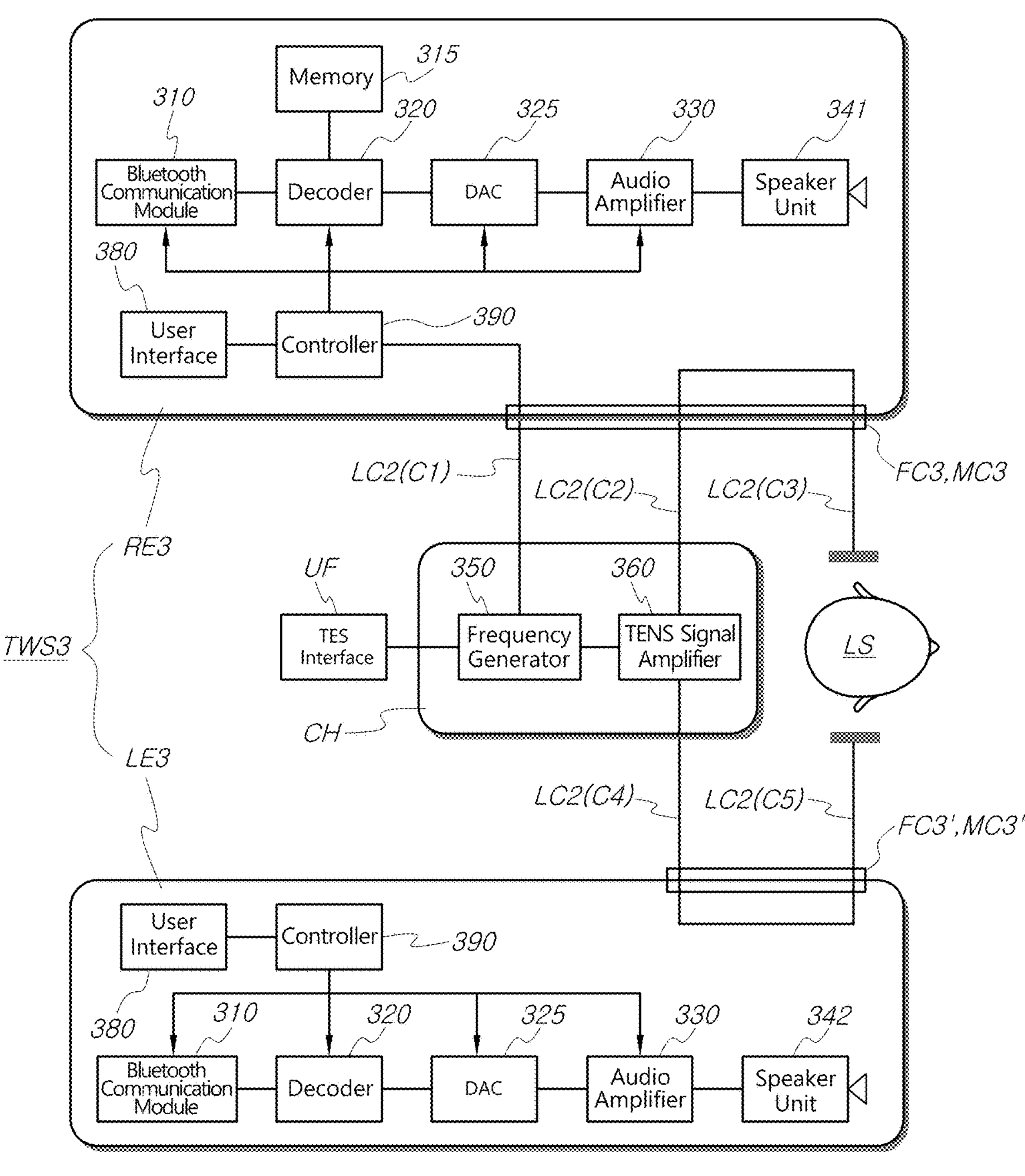
FIG. 11 is a block diagram of a circuit configuration of a modification of the second embodiment of the present disclosure.

If necessary, as illustrated in the earphone RE3 in the right portion of FIG. 11, an auxiliary battery B for charging the pair of left and right earphones RE3 and LE3 may be further provided in the cable housing CH of the link cable LC2 to be used as a power source for controlling the frequency generator 350, the TES signal amplifier 360, and the TES interface for the TES treatment, thereby allowing the simplest configuration of the TWS earphone assembly TWS3 with a TES treatment.

Alternatively, the battery life of the earphones RE3 and LE3 can be further increased with the auxiliary battery B, or the earphones RE3 and LE3 can be charged by connecting the earphones RE3 and LE3 with the link cable LC2.

What is claimed is:

1. A TWS earphone assembly comprising:

a pair of left and right earphones electrically separated from each other, each of the earphones including a housing and a circuit configuration accommodated in the housing, the circuit configuration comprising a Bluetooth® communication module, memory, a decoder, a digital-to-analog converter, an audio amplifier, a speaker unit, and a controller controlled by a user interface and configured to selectively execute a transcranial electrical stimulation (TES) treatment;

a frequency generator configured to generate low-frequency signals for TES treatment and a TES signal amplifier configured to amplify the generated low-frequency signals, the frequency generator and the TES signal amplifier being provided in one of the pair of left and right earphones;

an electrode provided on an outer surface of each housing of the pair of left and right earphones for electrical contact with a skin of a user's ear; and a pair of female connectors provided in the each housing of the pair of left and right earphones; and a link cable configured to be electrically and selectively connected to and disconnected from the pair of female connectors, wherein, when the link cable is electrically disconnected from the pair of earphones, the pair of earphones are configured to play back audio as TWS earphones, and wherein, when the link cable is electrically connected to the pair of earphones, the pair of earphones are configured to conduct the generated low-frequency signals between the electrodes so as to, in response to a user input selecting a first mode for the TES treatment or a second mode for the TES treatment with an audio playback, perform the TES treatment alone or to perform the TES treatment and the audio playback simultaneously.

2. The TWS earphone assembly of claim 1, wherein the link cable is one of a flexible electric conductive synthetic resin-coated and fiber-coated cable, a steel band that accommodates an electric wire therein, a synthetic resin band, a rubber band, and a spring wire band.

3. The TWS earphone assembly of claim 1, wherein the connectors are any one of a jack-plug, a USB-C type terminal, and a magnetic contact terminal.

4. A TWS earphone assembly comprising:

a pair of left and right earphones electrically separated from each other, each of the earphones including a housing and a circuit configuration accommodated in the housing, the circuit configuration comprising a Bluetooth® communication module, memory, a decoder, a digital-to-analog converter, an audio amplifier, a speaker unit, and a controller controlled by a user interface and configured to selectively execute a transcranial electrical stimulation (TES) treatment;

a pair of female connectors provided in the each housings of the pair of left and right earphones;

a link cable configured to be electrically and selectively connected to and disconnected from the pair of female connectors;

an electrode provided on an outer surface of each housing of the pair of left and right earphones for electrical contact with a skin of a user's ear; and a housing provided on the link cable, the housing including a frequency generator configured to generate low-frequency signals for the TES treatment and a TES signal amplifier configured to amplify the generated low-frequency signals, wherein when the link cable is electrically disconnected from the pair of earphones, the pair of earphones are configured to play back audio as TWS earphones, and wherein when the link cable is electrically connected to the pair of earphones, the pair of earphones are configured to conduct the generated low-frequency signals between the electrodes so as to perform the TES treatment alone or simultaneously the TES treatment with an audio playback.

5. The TWS earphone assembly of claim 4, wherein the link cable is one of a flexible electric conductive synthetic resin-coated and fiber-coated cable, a steel band that accommodates an electric wire therein, a synthetic resin band, a rubber band, and a spring wire band.

6. The TWS earphone assembly of claim 4, wherein the connectors are any one of a jack-plug, a USB-C type terminal, and a magnetic contact terminal.

* * * * *